United States Patent [19]
Stewart et al.

[11] Patent Number: 5,476,501
[45] Date of Patent: Dec. 19, 1995

[54] SILICON INSULATED EXTENDABLE/RETRACTABLE SCREW-IN PACING LEAD WITH HIGH EFFICIENCY TORQUE TRANSFER

[75] Inventors: Mark T. Stewart, Brooklyn Center; Mary M. Morris, Mounds View; Edward Di Domenico, Anoka; Kenneth W. Keeney, Forest Lake; Douglas R. Hess, Maple Grove, all of Minn.

[73] Assignee: Medtronic, Inc., Minneapolis, Minn.

[21] Appl. No.: 239,006

[22] Filed: May 6, 1994

[51] Int. Cl.$^6$ ........................................... A61N 1/05
[52] U.S. Cl. ........................................ 607/127; 604/265
[58] Field of Search ............................. 607/122–127; 128/642; 604/96, 97, 265, 280–282

[56] References Cited

U.S. PATENT DOCUMENTS

| | | |
|---|---|---|
| 4,106,512 | 8/1978 | Bisping . |
| 4,692,347 | 9/1987 | Yasuda ........................... 427/40 |
| 4,718,907 | 1/1988 | Karwoski ........................ 623/12 |
| 4,886,074 | 12/1989 | Bisping . |
| 4,976,720 | 12/1990 | Machold et al. ............ 604/96 X |
| 5,133,422 | 7/1992 | Coury . |
| 5,244,654 | 9/1993 | Narayanan .................. 604/96 X |
| 5,308,319 | 5/1994 | Ide et al. ..................... 604/96 X |

*Primary Examiner*—William E. Kamm
*Assistant Examiner*—Jeffrey R. Jastrzab
*Attorney, Agent, or Firm*—Daniel W. Latham; Harold R. Patton

[57] ABSTRACT

An implantable electrode type lead assembly of the flexible type which is particularly adapted for implantation in the cardiac tissue for applications such as use with a pacemaker. The lead assembly has an electrode head which includes a fixation spiral for implantation into tissue. The spiral or rotation action of the electrode head is controlled by means of an elongated torsionally wound electrical coil conductor, the coil extending through the lead from the proximal to the distal end thereof and carried within a silicone tube which is co-extensive therewith, the tube having been especially treated to modify the slip characteristics of the internal diameter (ID) thereof for high efficiency torque transfer.

11 Claims, 8 Drawing Sheets

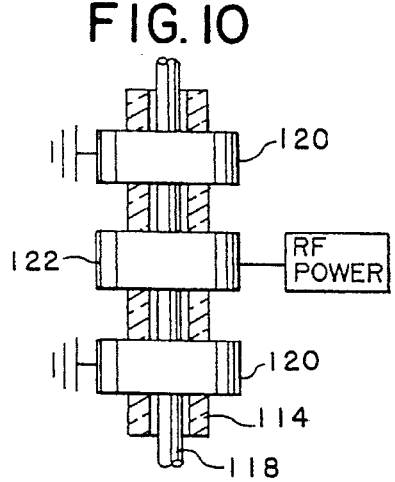
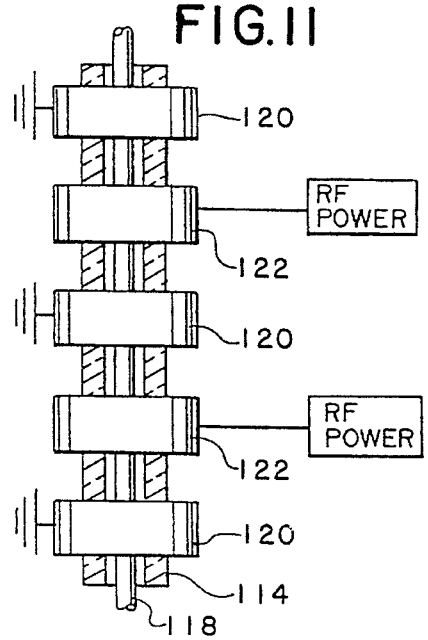
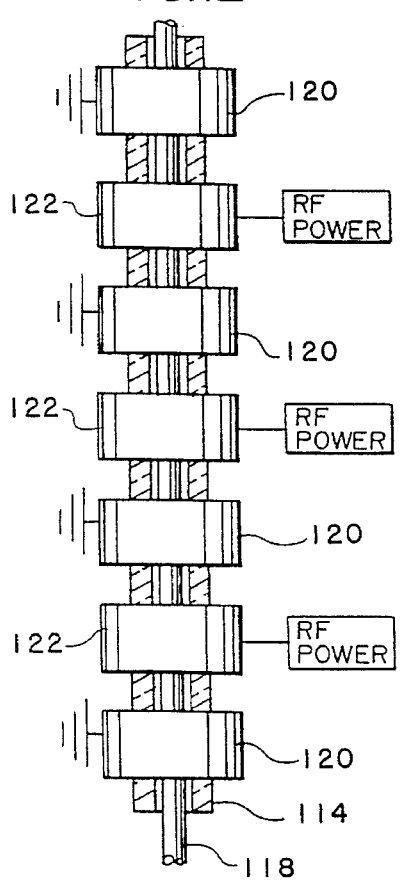
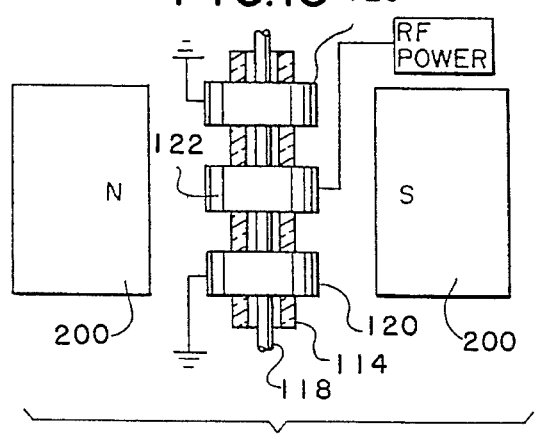
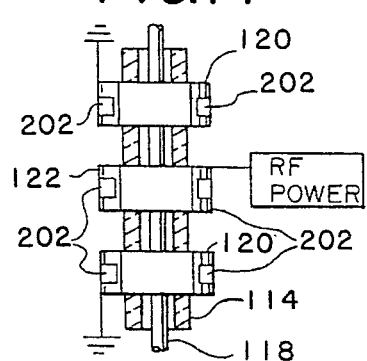
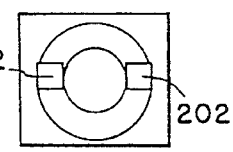

SILICON INSULATED EXTENDABLE/RETRACTABLE SCREW-IN PACING LEAD WITH HIGH EFFICIENCY TORQUE TRANSFER

BACKGROUND OF THE INVENTION

This present invention relates to a lead assembly including an electrode which is adapted for connecting a living organ to an electrical device. In the preferred embodiment shown herein the subject invention is adaptable for a pacing and sensing lead assembly which is transvenously implantable for electrically connecting a heart pacemaker device or generator with cardiac tissue.

In pacemaker technology and related arts, a body-implanted, intravascular lead assembly is oftentimes used which comprises an electrical conductor in a catheter-like construction, adapted at its proximal end to be suitably connected to a source of electrical energy, sometimes referred to as a generator or pacemaker. The assembly further includes an electrode means at the distal end of the conductor which is adapted to be secured to body tissue. With pacemakers, an intravenous transplantation method may be utilized to install the lead assembly. With this method, the electrode means is pushed into the heart through a blood vessel.

In the typical lead assembly for use in the above-purposes, the lead assembly of an electrical conductor and electrode means affixed to the end of the conductor is adapted to be firmly lodged in and permanently secured to and removable when desired from tissue inside the body at a desired location. The conductor and the portion of the electrode means affixed to the conductor are sealed from body fluids and tissue by a material substantially inert to body fluids and tissue. Means are provided for permitting the lead and electrode means to be inserted into and guided through a body vessel to a position inside the body without causing injury to the body vessel and for permitting the electrode means to be firmly lodged in and permanently secured to body tissue. The electrode of the lead assembly may be firmly anchored to tissue which is heart muscle by a helix of suitable electrode material within the sheath of the lead assembly, the electrode being rotated in corkscrew-like fashion for screwing the electrode into the tissue by rotating the conductor and thus rotating the helix of the electrode for affixation.

Lead assemblies of this type are disclosed in U.S. Pat. Nos. 4,106,512 and 4,886,074 to Bisping, incorporated by reference herein in their entirety, which have a flexible helical conductor whose end has a helix-like electrode. Commercial versions of such leads are adapted to make use of a rotational force exerted from the proximal end to cause rotational movement of the conductor such that it can cause the helix electrode to be either extracted from or screwed into the tissue against which it is brought to bear. With this type of lead assembly where the forces must be exerted from the proximal end, difficulties may be encountered in that, due to forces along the electrical conductor and the insulating sheath or tube carrying it, friction caused thereby may result in undue effort at the proximal end and loss of a substantial amount of that effort over the length of the conductor due to torsional absorbance, all of which is not particularly desirable.

Various sheath or tubing materials have been used to carry the elongated conductor such as polyurethanes or fluoropolymers. However, these materials lack the flexibility of silicone. Unfortunately, silicone possesses a tacky surface and is unable to provide low coil rotation resistance.

It is a primary purpose of this invention to lower and thereby improve the coil rotation resistance and slip characteristics of tacky silicone tubing to the point where it is more desirable for use in such devices than the other tubing materials. Long term benefits also accrue in that less cold flow of the silicone will occur over time, as during shelf life, tending to decrease likelihood of inner coil sticking to the tube.

SUMMARY OF THE INVENTION

The design of extendable/retractable screw-in pacing leads requires that a small diameter elongate torsional coil be able to rotate with low resistance (due to friction) within a length of polymeric insulation tubing. Previous screw-in leads built using polyurethane presented a lower coefficient of friction and contact with such wire coils but lacked flexibility. The tacky surface of silicone rubber tubing for this purpose causes excessive friction which makes coil torque transfer through the silicone tubing difficult. The use of higher durometer (harder) silicone helps some to alleviate this difficulty but the performance of such a lead is still marginal.

Also, some present leads using polyurethane tubing have been known to oxidize and therefore lose their mechanical and insulative properties. To prevent this degradation the metal coils have been coated with precious metals which adds to the cost of the devices.

It is, therefore, a purpose of this invention to use silicone tubing in the manufacture of retractable screw-in cardiac pacing leads and other similar leads wherein the silicone tubing has been especially treated to improve its slip characteristics, particularly in the inside diameter (ID) thereof.

BRIEF DESCRIPTION OF THE FIGURES

FIGS. 10, 11 and 12 are schematic representations of reactors incorporating multi-segment electrodes with 3, 5 and 7 electrode rings, respectively;

FIG. 13 is a schematic representation of a reactor electrode system incorporating an electromagnet; and, FIG. 14 is a schematic representation of a reactor electrode system incorporating permanent magnets in the electrodes, FIG. 14a being a top view of an electrode ring with embedded magnets.

DETAILED DESCRIPTION OF THE PREFERRED EMBODIMENT OF THE INVENTION

Currently, extendable/retractable pacing leads are usually constructed from polyurethane tubing which provides a low friction surface for carrying the elongated conductor coil to rotate inside the tubing. The extendable/retractable screw-in pacing lead utilizes a helix (lead tip electrode) which is screwed into the heart tissue remotely by the physician. When the lead is properly situated in the desired heart chamber, the physician turns the connector end of the lead in order to rotate the inner coil conductor to thereby extend and screw the helix into the heart tissue. To meet user requirements, this screw-in feature requires low frictional losses during rotation of the inner coil in the tube carrying it otherwise as many as about twenty turns may be needed. In accordance with this invention, silicone tubing is utilized within the lead which has been especially plasma treated to lower the friction within its lumen thus allowing silicone tubing to be used for the construction of a fully functional screw-in lead.

Figure 1:
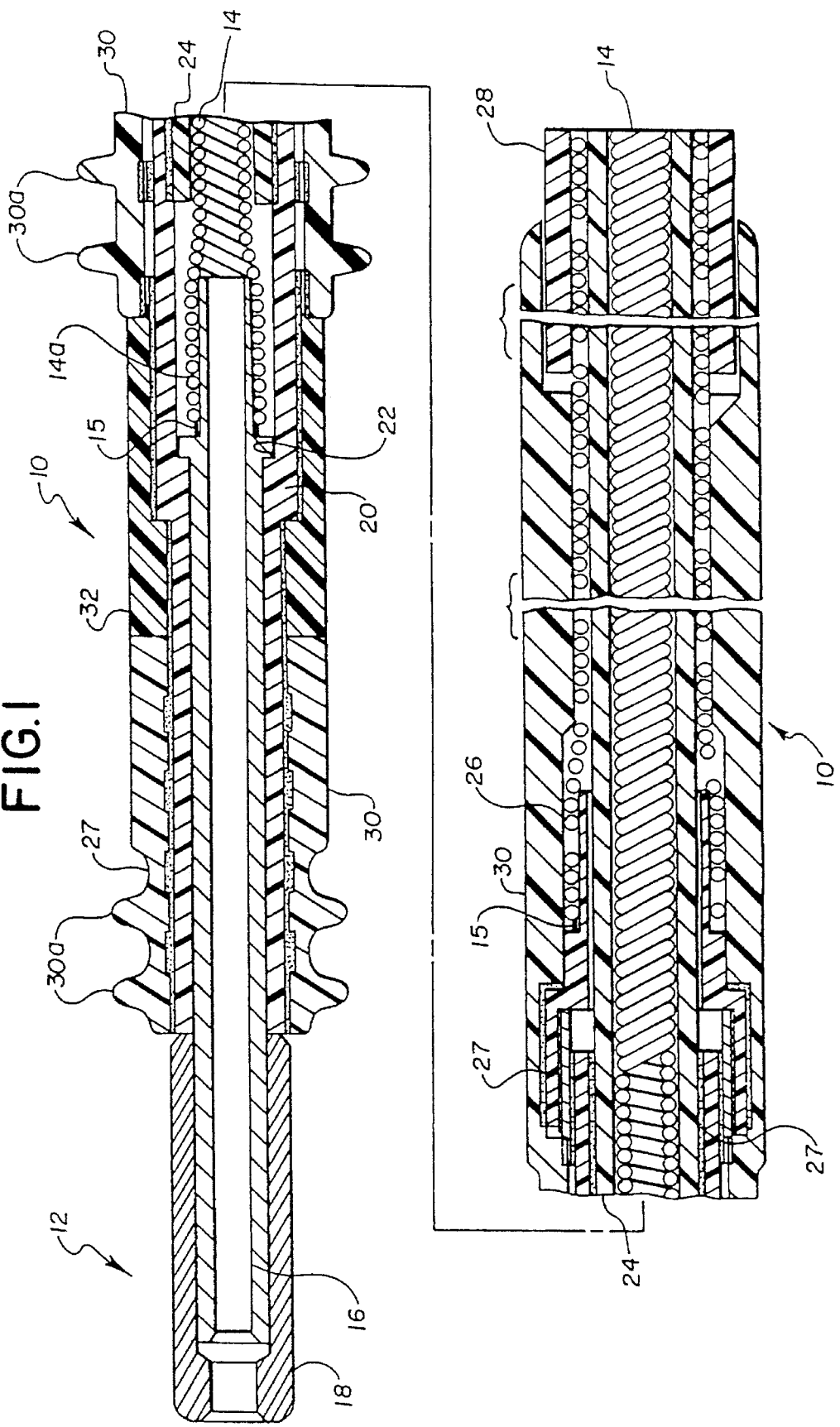
FIG. 1 is a partial side cross-sectional view of the proximal end of an electrode lead assembly according to the invention.

Referring first to FIG. 1, a preferred lead assembly, generally designated 10, has a distal end, generally designated 12 and an electrically conductive wound electrical coil conductor 14 centrally positioned within lead 10 and extending longitudinally substantially throughout its entire length. Distal end 14a of coil conductor 14 is attached, as by a laser weld 15, to a pin 16 which in turn is connected to an end cap 18. Pin 16 is free to rotate within a rigid polyurethane body 20 which has a bearing surface 22 to facilitate rotation of pin 16 and cap 18 which effects rotation of conductor coil 14 over its entire length. Pin 16 and end cap 18, in addition to providing a means for the physician to rotate the coil within the lead also serves as a connector for plugging into an implantable generator or the like by means of which electrical connection between coil 14 and the generator (not shown) can be established. Coil 14 is shown carried in a length of inner silicone tubing 24 which extends co-extensively with coil 14 over substantially the entire length of lead 10. The inner diameter (ID) of tubing 24 is especially treated to improve its slip characteristics by plasma treatment which is described more fully hereinbelow.

If the lead is of the bi-polar type, a return conductor coil 26 will also be included as shown. However, it may be uni-polar or bi-polar, etc. All of the aforementioned elements are carried in an outer silicone tubing 28, the distal end of which may be received in a molded silicone sleeve 30 which terminates at its distal end in a seal configuration 30a, two pairs of which are provided at spaced distances providing therebetween the distal housing portion 32 of lead 10.

Figure 2:
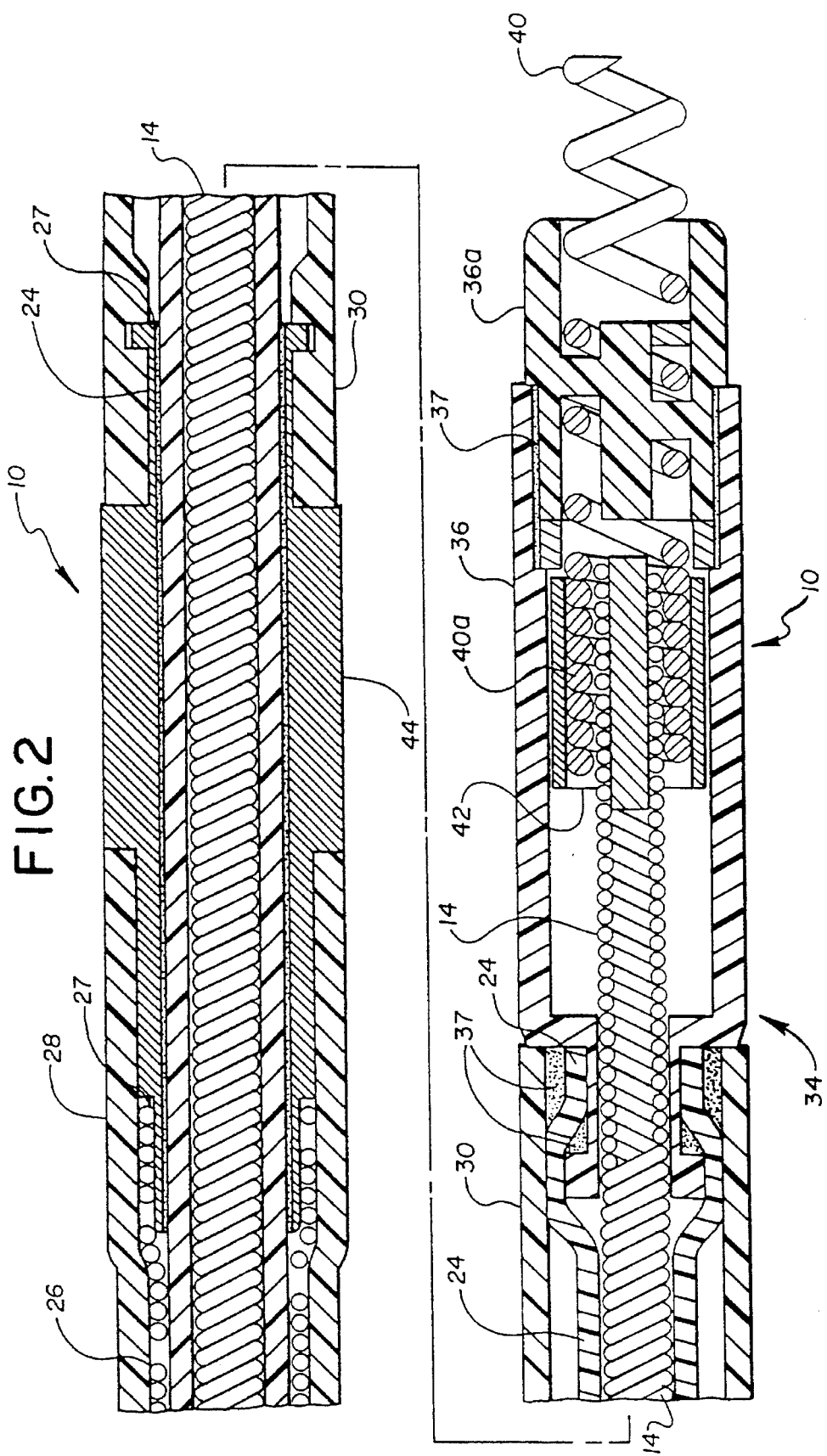
FIG. 2 is a similar view of the distal end of the electrode showing the helix electrode extended as it would be for insertion into tissue; and, FIG. 3 is a view similar to that of FIG. 2 showing the helix electrode in its retracted position.

Referring now to FIG. 2, the distal end generally indicated at 34 of lead 10 is shown. The elements of FIG. 1 which are shown in FIG. 2 carry the same numeral legends as in FIG. 1.

Figure 3:
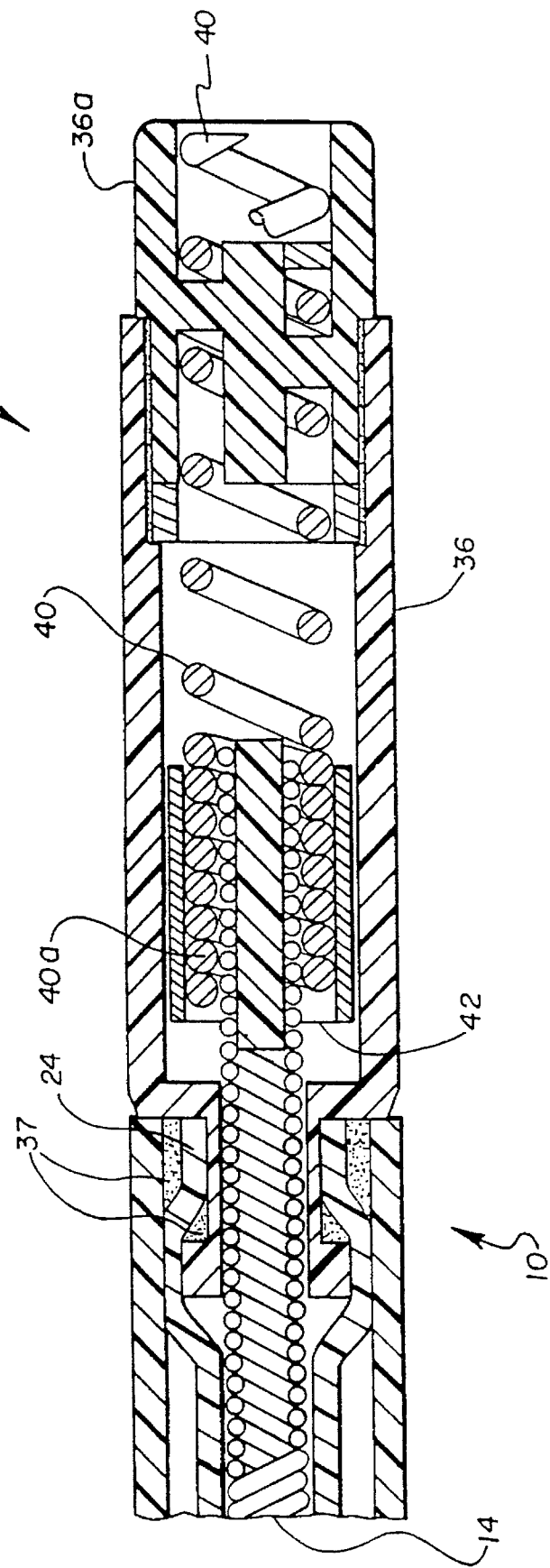

The proximal end of inner silicone tubing 24 is shown attached to one end of a rigid body 36 such as polyurethane as by suitable adhesive 37, such as a silicone adhesive. The distal end of inner conductor coil 14 extends through the proximal end of body 36 which acts as a bearing surface for coil 14's rotation. Rigid polyurethane 36 is constructed and arranged as shown to carry a screw-in helix electrode 40 which may be rotated through end body portion 36a to be extended as shown in FIG. 2 or retracted as shown in FIG. 3. Body 36 and body 36a may be secured by a suitable adhesive 37 as shown. Helix electrode 40 is attached to rotatable coil conductor 14 as by crimping about the end of conductor 14 as shown. The crimped portion thereof at 40a may be carried in a floating sleeve 42 to further facilitate rotation.

Since lead 10 is of the bi-polar type it will also include a blood contact electrode 44 which connects to return conductor coil 26, as by a laser weld 27, to provide for a return conductive path in the lead toward the proximal end. Electrode 44 is fastened into the lead by means of a layer 27 of suitable adhesive such as a silicone adhesive.

As already noted, in FIG. 3, helix electrode 40 is shown in its fully retracted position. Similar elements of the lead have been given the same numeral legends as they carry in FIGS. 1 and 2.

The treatment of the silicone tubing comprises a plasma reactor and method which produces a glow discharge within the lumen of small diameter silicone tubing for the purpose of cross-linking and hardening the inner surface. This is described in application entitled *PLASMA PROCESS FOR REDUCING FRICTION WITHIN THE LUMEN OF POLYMERIC TUBING* filed of even date herewith Ser. No. 08/239,007 the entire content of which is incorporated herein by reference.

This treatment is preferably performed continuously meaning that tubing is fed from a spool of 1,000+ feet of tubing and treated, in one preferred embodiment, as it moves through an outer glow discharge zone and then an inner glow discharge zone of the reactor apparatus after which it passes into a receiving chamber. This inner ID glow discharge or inner treatment zone includes a set of radio frequency electrodes or a microwave cavity. Inside the electrodes is a section of glass tubing serving as a reactor, the tubing having an inside diameter of, for example, approximately 2 to 7% (about 5–7% being most preferred) greater than the outside diameter of the silicone tubing which is being treated within the glass reactor. This is required in order for the glow to be preferentially produced inside of the silicone tubing. When a space of greater than about 0.006 inch or about 7% exists between the silicone and glass reactor, undesired discharge may occur in the space around the outside of the tubing and within the glass reactor rather than preferentially inside of the silicone tubing only. In a separate zone of the apparatus, located just prior to the inner treatment zone i.e., an outer glow discharge zone or outer treatment zone, the outside of the silicone tubing may be glow discharge treated to reduce friction between the OD of the silicone tubing and the inside surface of the glass reactor, which may occur as the silicone tubing passes through the inner treatment zone's small diameter glass reactor. This outer treatment zone may consist of a 0.5 inch or larger glass tube around which is a set of radio frequency electrodes, a coil or a microwave cavity used to excite a glow discharge around the outside of the plastic tubing. In the case of very small tubing, treatment on the outside first can be very important to prevent the tubing from sticking to the close fitting reactor in the ID treatment zone.

All of these glow discharge treatments both inside and outside of the polymeric tubing described above may involve the use of "inert" gases such as helium, neon, argon, or nitrogen. However, residual air contained within the tubing will produce discharge as well since it is primarily nitrogen. Gas pressure in the upper section of the reactor is preferably maintained at a relatively higher pressure than the OD treatment section, although this is not necessary. This fills the plastic tubing with gas to a stable pressure while the OD zone is maintained at a relatively lower pressure which is usually more desirable for the outer surface plasma treatment. Pressure differentials are not critical but can be desirable. These differential pressures are maintained by using gas flow controls, orifices, and automatic exhaust valve pressure controllers (not shown in any detail).

In a variation on the above treatment, a polymerizable siloxane vapor (e.g. hexamethyldisiloxane) has been introduced into the upper chamber of the apparatus. This vapor polymerizes on the outside of the tubing in the outer treatment zone producing a very smooth low friction surface. More importantly, some of the siloxane vapors permeate the tubing wall and pass into the inner treatment zone where they become polymerized as a coating inside of the tubing as well. This means that it is also possible to deposit plasma polymers inside of silicone tubing without feeding the vapors through the end of the tube which would be impractical in long, small diameter tubing. U.S. Pat. Nos. 4,718,907 and 4,692,347 reports on systems in which silicone tubing having a length to diameter ratio of less than 100 were coated inside with plasma polymers when vapors were fed into the end of the tube. On the other hand, the length to diameter ratio of the tubing treated could be, for example, 37,500.

In another sense, the tubing having modified slip characteristics on the inside surfaces thereof particularly small diameter silicone tubing of less than about 1 mm in OD. This is accomplished by means of plasma discharge within the tubing. Improved apparatus for accomplishing this is also provided.

Figure 4:
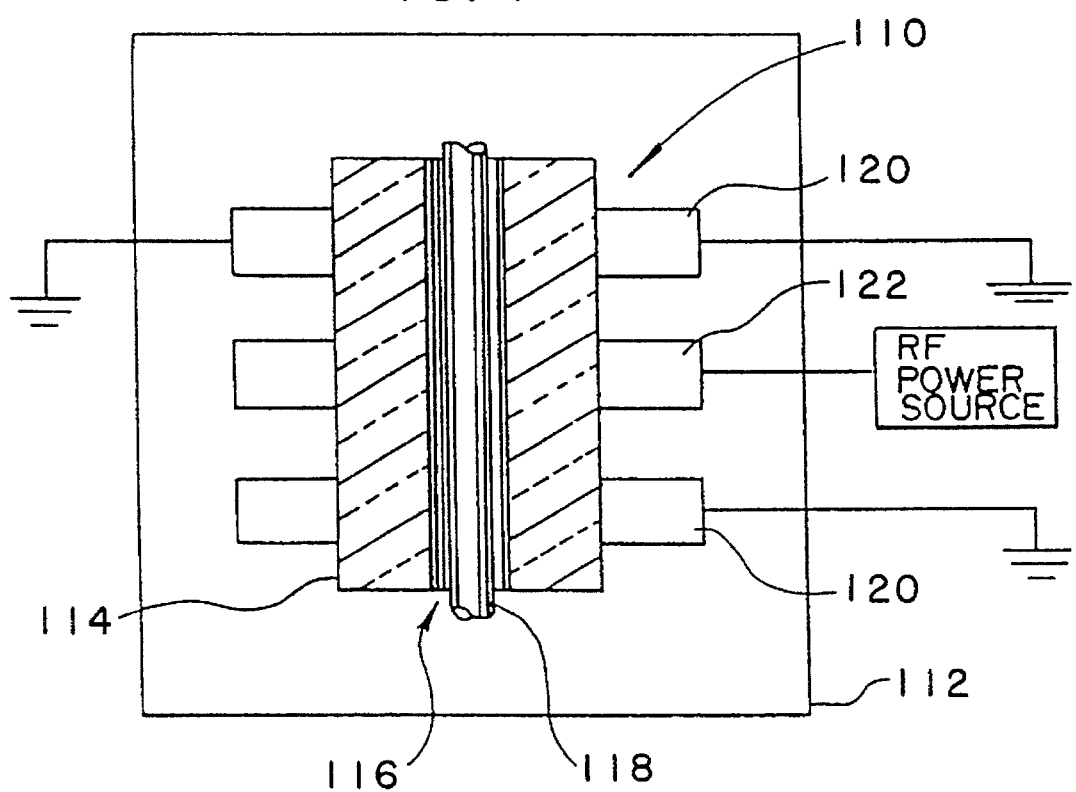
FIG. 4 is a schematic arrangement showing how a piece of polymeric tubing is held in an appropriate glass reactor with minimal clearance while being subjected to plasma discharge.

Reference to FIG. 4 schematically shows how this can be accomplished. Plasma discharge apparatus generally indicated at 110 is enclosed within an evacuated environment 112 which may contain an inert plasma discharge gas such as nitrogen, helium, neon, argon or the like, at a suitable pressure for discharge such as 0.6 torr. Such gases are known to provide, under plasma discharge conditions, cross-linking and hardening of polymer and dielectric surfaces. Preliminary figures for the improvements in slip characteristics indicate that the coefficient of sliding friction between the interior of a silicone tube and metal (e.g. a stainless steel needle) can be reduced by 40–70% by the treatment of the present invention. Herein, these inert gases are referred to as non-film forming gases. Nitrogen is presently preferred for this embodiment.

On the other hand, if it is desired to even more markedly modify the slip characteristics of the surface, a film-forming gas which will polymerize under plasma discharge conditions may be used. Such gases include volatile monomers such as the various hydrocarbons. Siloxane is particularly preferred when working with silicone rubber at the present time. Mixtures of these gases with the non-film forming gases also provide coatings.

Discharge apparatus 110 of FIG. 4 includes a glass reactor and holder 114 having a bore 116 therethrough. A glass capillary tube serves well for this purpose in the case of small polymer tubing. Inside bore 116 is a length of silicone tubing 118 of relatively small ID and OD, as mentioned hereinabove. The bore 116 has an inside diameter of about 2 to 7% greater (not to exceed about 0.006 inch) than the outside diameter of the silicone tubing 118 to be treated. Generally, the bore 116 may be sized about 3 to 5 thousandths of an inch larger than the silicone tubing. As already indicated, close fit and small clearance are required in order to prevent glow discharge from occurring around the outside of the tubing. If this exterior discharge occurs, it extinguishes the discharge inside the tubing which is to receive treatment. The dimensions above are exemplary of effective dimensions which accomplish the end of preferential ID discharge under conditions of suitable pressure, type of gas and size of chamber, etc. However, in any given instance empirical adjustments will determine the relationships necessary to achieve preferential discharge inside the tubing. This unique stratagem enables one to preferentially sustain plasma discharge inside tube 18 with no discharge occurring on the outside of the tubing 118. This has been found to provide uniform surface modification in even small size tubing. Specifically, a reactor apparatus has been run with a 0.059 inch ID bore glass capillary tube (0.315 inch OD) for treatment of 0.054 inch OD silicone tubing. For tubing less than about 1.5 mm, such as this 0.054 inch tubing, it is essential if treatment is carried out in apparatus like FIG. 4 on a continuous basis that the OD of the tubing be pretreated to avoid sticking of the tubing to the glass reactor.

Still referring to FIG. 4, two circular, donut shaped ground electrodes 120 and an RF powered electrode 122 encircle glass reactor 114 as shown. The RF power is preferably operated in a pulse mode. For example, it has been found that pulsing between about 300 watts and about 80 watts for 1–4 milliseconds and 1–10 milliseconds, respectively, produce effective discharge within a relatively small tube such as is shown at 118 without overheating. As already noted, for very small tubing less than 1 mm ID the pulsing is essential.

In an arrangement such as that shown in FIG. 4, if the length of the tubing 118 is greater than the length of the discharge zone between the electrodes 120 and 122, it will be desirable to make provisions to provide discharge throughout the entire length of the tubing. This may be accomplished in a variety of ways. For example, additional sets of electrodes can be distributed over the length of the apparatus. Also, an arrangement may be provided (not shown) in which the set of electrodes move over the length of the apparatus. Most preferably, the arrangement will be modified to allow the tubing 118 to move through the bore 116 as by being pulled therethrough thus passing the tubing through the discharge zone which exists between the electrodes. An embodiment of this latter preferred arrangement is shown schematically in FIG. 5. Continuous tension is preferred to avoid having the polymeric tube stick in the reactor.

Figure 5:
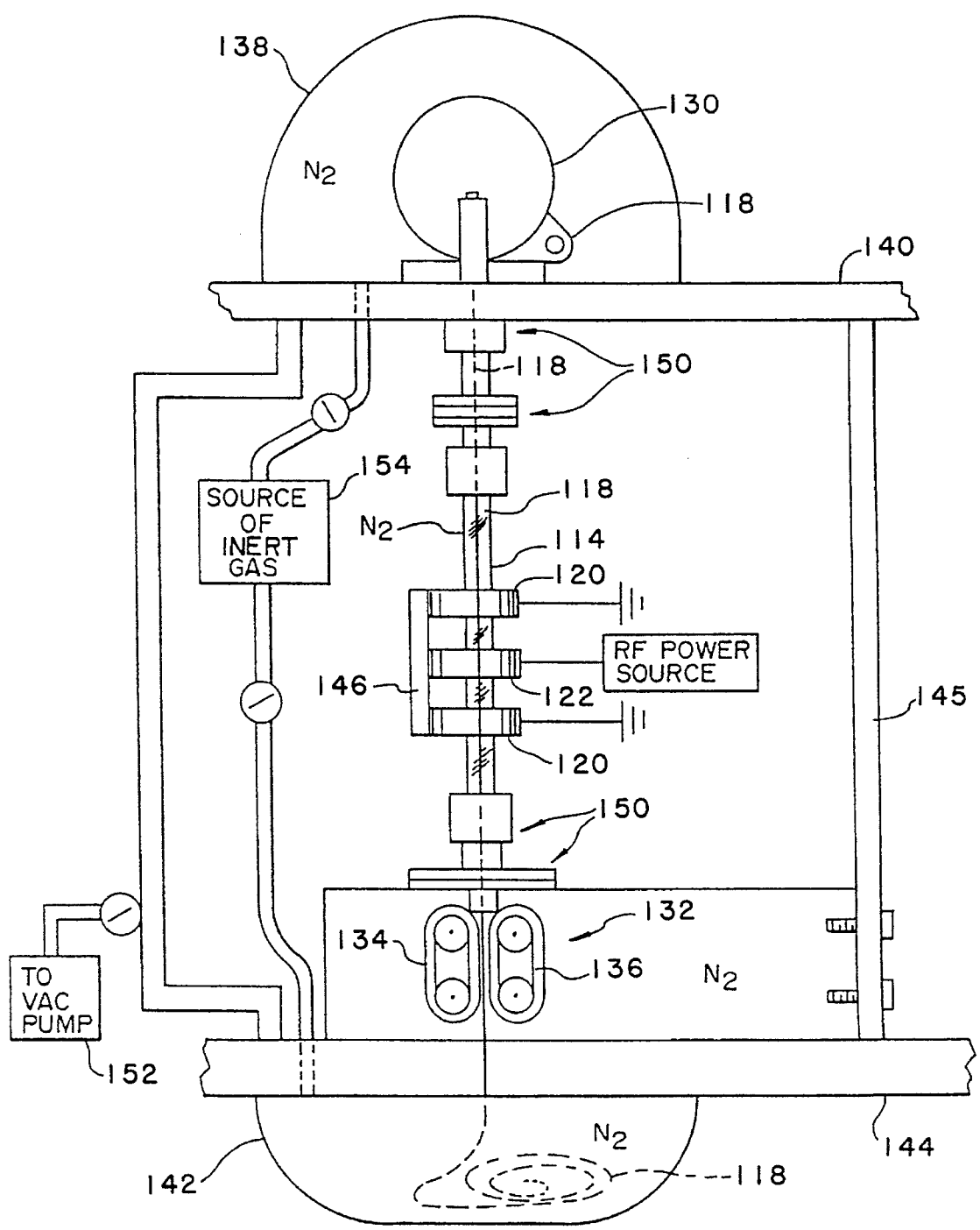
FIG. 5 is a showing of an apparatus for plasma discharge treating a coiled length of tubing preferentially on its ID on a continuous basis.

The apparatus of FIG. 5 is designed to take advantage of the permeability of silicone rubber for the purpose of conveniently introducing the discharge gas into the inside of the tubing to be treated. In this apparatus a supply of the tubing 118 is held on a reel 130 at the top of the apparatus from which it is pulled by a means such as a tubing transport track drive generally indicated at 132 which is positioned at the bottom of the apparatus. The track drive may include a pair of electrically driven controlled speed drive belts 134 and 136. Other arrangements for pulling the tubing through the apparatus will be apparent to those familiar with this art.

Reel 130 and the supply of tubing it carries are maintained within a sealed environment by means of a bell jar or the like 138 which seals against an upper plate 140. Likewise, the treated tubing which is collected at the bottom of the apparatus is contained within a sealed environment provided by bell jar arrangement 142 which seals against bottom plate 144. Other means for providing sealed chamber arrangements will be readily apparent to those familiar with this art.

In the arrangement of FIG. 5, the primary component is the glass capillary tube reactor 114 through which the silicone tubing 118 passes. ID surface modification is accomplished by the plasma discharge inside the silicone tubing, which occurs in the vicinity of the electrodes 120 and 122 as the tubing passes through the plasma discharge zone (about 1–15 feet/min. is preferred). The electrodes may be held in relative position by means of an insulator spacing holder 146 of PTFE or the like. Of course, the bore within glass capillary tube reactor 114 and the close fit of the plastic tubing therein are arranged in accordance with the discussion hereinabove to create preferential discharge within tubing 118.

In the apparatus, capillary tube 114 is sealingly held to the bottom of upper plate 140 and the top of bottom plate 144 by means of appropriately selected compression fitting and flange arrangements generally indicated at 150, as will be known to those familiar with this art. A side plate means 145 is included to interconnect top and bottom plates 140 and 144 thus rigidly fixing the compression fittings 150 together.

The gas environment is provided by evacuating bell jars 138 and 142 by means of a vacuum pump connected to outlet arrangement 152. Since capillary tube 114 is in sealed communication with both 138 and 142 the entire systems is evacuated in this manner. Other chamber designs may be used. The selected discharge gas, such as nitrogen ($N_2$) in this instance, is introduced to the system through inlet arrangement 154 to a pressure such as 0.6 Torr.

Due to the permeability of silicone rubber, tubing 118 absorbs gas as it remains on reel 130 in bell 138, the gas equilibrating within the tubing ID usually within an hour or so to fill the tubing so that, as the tubing passes through capillary tube 114, it carries the discharge gas with it into the discharge zone between the electrodes. If using tubing other than silicone, such other tubing not being as readily permeable, a standing time of a few hours allows the atmosphere of the chamber to permeate and/or to enter the tubing through its ends and equilibrate. Upon establishment of pulsed RF power such as that described with reference to FIG. 4, preferential discharge occurs within tubing 118 between the electrodes as the tubing passes from reel 130 to bell 142 for collection. In this manner surface modification of the slip characteristics of the ID of tubing 118 is effected, whether merely by hardening or by coating, as desired and depending on the type of gas used.

Due to the tacky nature of silicone rubber, an apparatus such as that shown in FIG. 5 may experience difficulty with the tubing 118 sticking in capillary tube reactor 114 as the tubing is pulled therethrough. Consequently, it is most preferred particularly in the case of small ID tubing, that the OD of the tubing be plasma discharge treated before the ID is treated so as to enhance the slip characteristics of the tubing OD and facilitate passage of the tubing through capillary reactor 114 for discharge treatment of the tubing ID. A preferred apparatus is discussed in connection with subsequent FIGS. 6–9. The apparatus includes three zones—an OD treatment zone 160, a transition zone 182 and an ID treatment zone 166 as are identified in FIG. 6.

Figure 6:
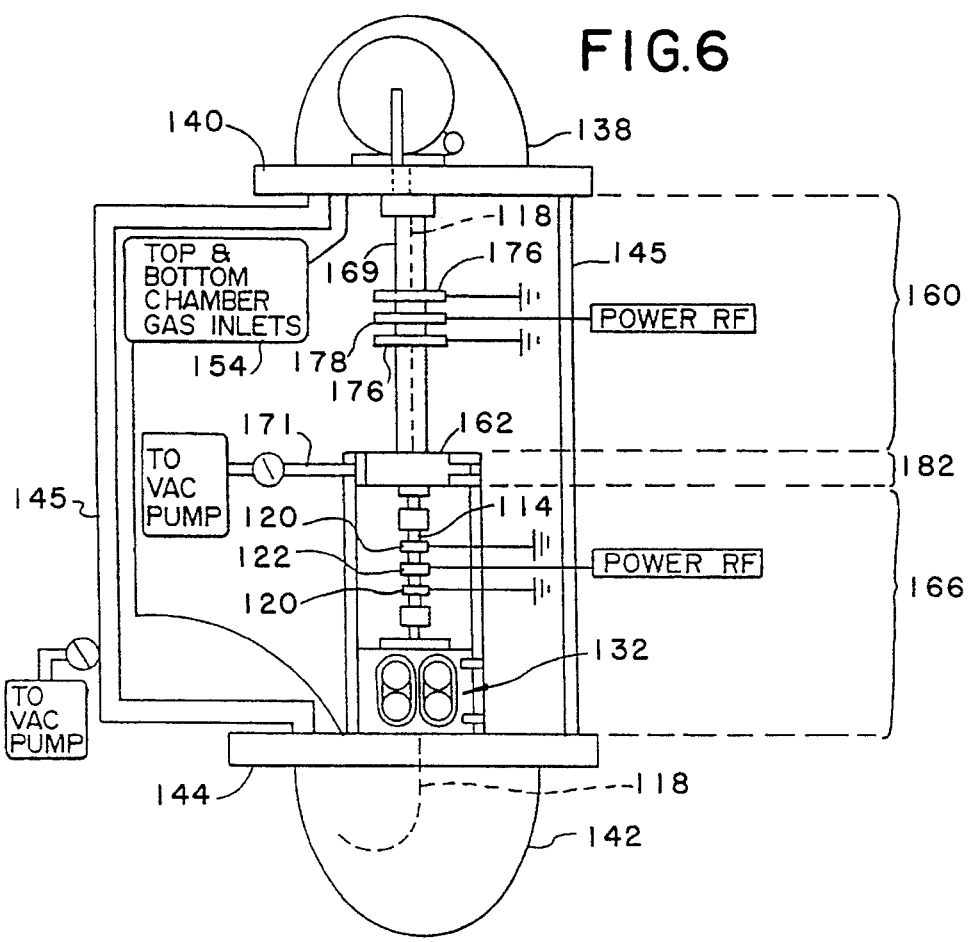
FIG. 6 is a showing of an apparatus similar to that of FIG. 5 but modified to additionally plasma discharge the OD of the tubing prior to its ID treatment.

Referring now to FIG. 6, the OD (outside diameter) zone 160 is the first plasma that the tubing 118 passes through after coming off of reel 130. The top of this section of the apparatus seals against the underside of the top plate assembly 140 as in FIG. 5. The bottom of this section seals against the "transition zone" block 162. In the OD zone 160 the tubing 118 receives a plasma treatment on its outer surface. The treatment is desired in order to reduce surface tackiness of the silicone tubing 118 for handling in the ID zone of the lower portion of the apparatus. This facilitates the tubing passage through a small diameter glass capillary tube 114 in the ID treatment Zone 166 without sticking to the glass.

Figure 7:
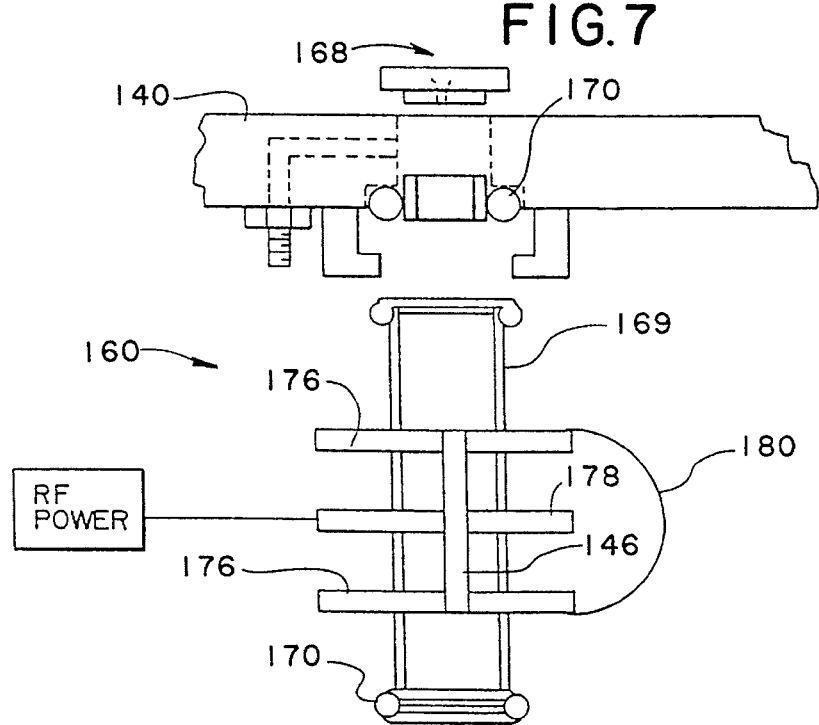
FIG. 7 is a detailed showing of the OD treatment zone of the apparatus of FIG. 6.

Upon entry into OD zone 160, the tubing may pass through a PTFE orifice 168, best seen in FIG. 7, which generally should have a diameter equal to the tubing nominal OD plus 0.001 in ±0.001 in. This diameter may vary depending on the type of tubing and type of treatment or coating to be performed. For tubing 0.054" OD the orifice should be drilled to about 0.055". This size may later be adjusted to achieve precise pressure differentials. The orifice serves to a) prevent the glow discharge from spreading into the upper tubing reel chamber, b) allow different pressures or types of gasses to be maintained in the upper chamber 138 and OD zone 160, c) guide the tubing 118 down the center of the OD zone 160, and d) allow a small gas flow from the upper chamber 138 to the OD zone tube 169 below where a vacuum exhaust line 171 may be arranged to carry away the flow.

The OD zone 160 may consist of a section of glass tubing 169 which is commonly available such as 1.5 inch diameter, sanitary glass tubing. The length of the OD tube 169 may typically be between 6 and 18 inches in length. The glass tube 169 should be capable of forming a vacuum seal with each end of the tube butting up against a O-ring 170, see FIG. 7. Provision is made to allow for entry of gases below the orifice 168 and above the end of the glass OD tube section 169.

The reason for the OD of the glass 169 being preferably about 1.5 inches is that in a smaller tube such as 0.5" inches the silicone tubing must be substantially centered in order to maintain a uniform glow discharge at lower gas pressures. The larger tube tolerates more misalignment and maintains a uniform discharge around the tubing.

The circular disc or donut shaped electrodes 176 and 178 are dimensioned to suit the diameter and length of the OD tube 169. A PTFE insulator support bar 146 may be included as shown in FIG. 7. The two ground electrodes 176 may be connected by a common ground strap 180 also as shown in FIG. 7.

Figure 8:
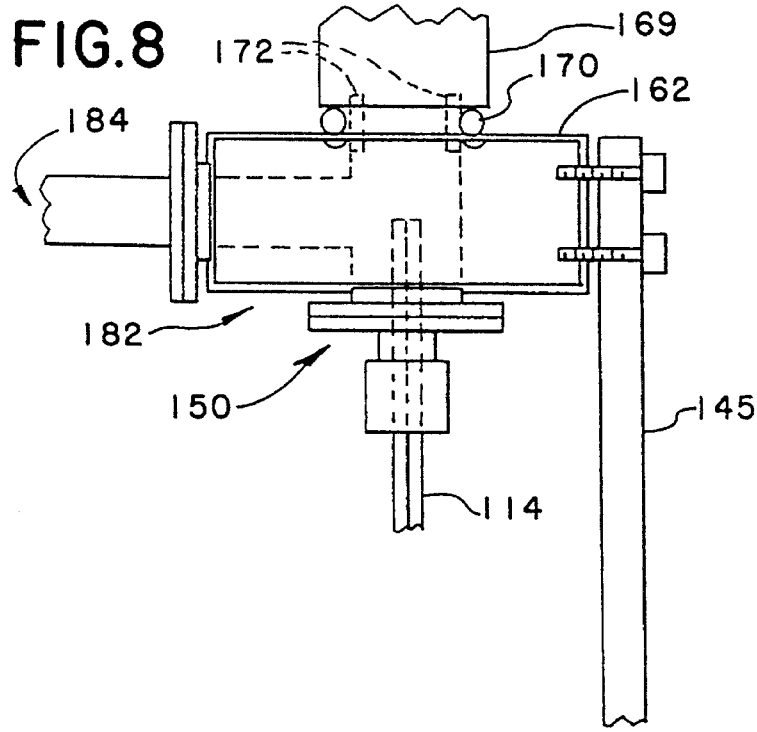
FIG. 8 is a detailed showing of the transition zone between the OD and ID treatment zones of the apparatus of FIG. 6.
Figure 9:
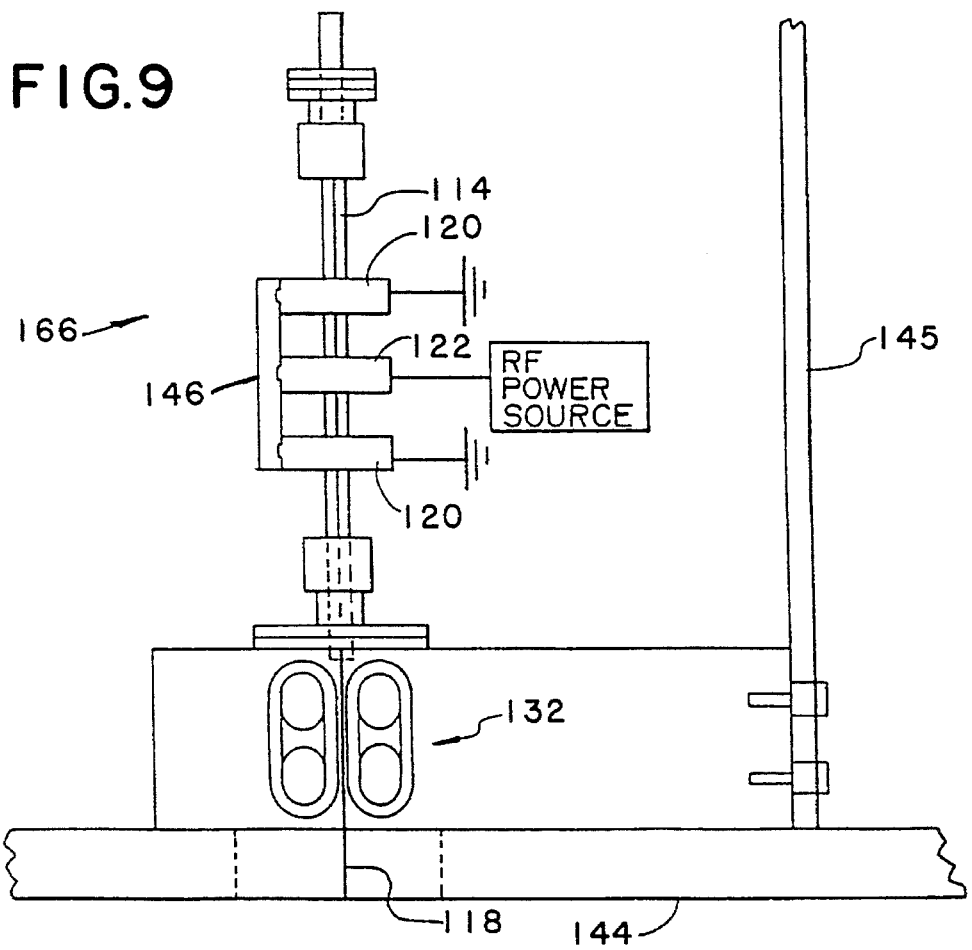
FIG. 9 is a detailed showing of the ID treatment zone of the apparatus of FIG. 6.

Transition Zone, zone 182—see FIG. 8 in particular, serves as a connection between the OD and ID treatment zones 160 and 166, respectively. It must a) be capable of forming a vacuum seal with the lower end to the OD treatment glass tube 169, b) connect with the compression fitting 150 of the ID treatment zone 166 below it—see FIG. 8, c) provide a vacuum port 184 which connects to an automatic throttle valve pressure controller (this allows gas flow which enters through or below the orifice 168 at the top of the OD zone 160 to be drawn off below the OD zone), and d) provide a rigid connection to the lower end of the ID treatment zone 166 in order to minimize or prevent any relative motion between the top and bottom compression fittings 150 of the ID treatment zone 166.

The Inside Diameter Treatment Zone, zone 166—see FIG. 6 in particular, performs the glow discharge treatment of the inside of the tubing 118 as it moves through the zone, similar to that shown in FIG. 5. The primary component is the glass capillary tubing 114 through which the silicone tubing passes. The slip treatment on the tubing outer surface which is performed in the OD glow discharge zone 160 prior to entry into the glass capillary tube is recommended to prevent the silicone tubing from sticking to the glass. The tubing must pass through the glass capillary without binding for ease of handling.

The glass capillary reactor 114 or equivalent is a critical component. The small bore in the glass is sized approximately 2 to 7% larger than the silicone tubing that will be treated. The small clearance is required in order to prevent glow discharge from occurring around the outside of the silicone tubing as already stated.

Length of the capillary 114 should generally be as short as possible about 3" of exposed glass between compression fittings is the practical minimum with the apparatus shown to still allow the donut shaped electrodes 120 and 122, (3 capacitive rings) enough room. If multiple (more than 3) capacitive electrode rings are used, a length of 4–6 inches may be required. Also, if a helical resonator plasma excitation (13.56 Mhz) source is used, a tube length of close to 10 inches may be required.

Electrode configuration may vary. However, this will have little effect on the design of the mechanical components of the apparatus. If 3, 5, or 7 capacitive ring electrodes are used, the only design change between them will be an adjustment of the length of the capillary tube 114. For present purposes three sets of silver plated brass electrodes are being used successfully. If a helical resonator source (not shown) is used instead of capacitive electrodes, sufficient space must be reserved around the capillary tube. This source may be positioned co-axially around the capillary tube and may have a cylindrical shape incorporating an RF resonant coil and cavity with a diameter of about 5 inches and a length of 6–10 inches.

Various electrode configurations can be used. They all provide the best performance when pulsed RF power is used. As can be seen in FIGS. 10–12, segmented electrodes consisting of 3, 5, 7 or more cylindrical segments may be used to act in combination to concentrate the electric field inside of the tubing lumen.

A reactor apparatus can readily achieve low pressure discharge within very small diameter and multi-lumen tubing by using magnetically enhanced electrode(s). Examples of such enhanced electrode assemblies are shown in FIGS. 13, 14 and 14*a* utilizing electromagnets 200 and permanent magnets 202 respectively, FIG. 14*a* representing a top view of an electrode ring 120 or 122 from FIG. 14 with embedded magnets 202. All of these aspects are akin to magnetic confinement of the plasma with the tubing lumen.

While there has been shown and described what is considered to be a preferred embodiment of the present invention, it will be apparent to those skilled in the art that various changes and modifications of the lead may be made herein without departing from the invention as defined in the appended claims.

What is claimed is as follows:

1. In an elongated medical device including a length of tubing defining an elongated passageway therethrough, said passageway having a surface of silicone rubber, and a rotatable metal insert extending the length of the passageway and bearing against the silicone rubber surface thereof for rotation therein, the silicone rubber surface having a friction with the rotatable metal insert, wherein the improvement Comprises a modified silicone rubber surface provided against the rotatable metal insert, said modified silicone rubber surface improved with respect to the slip characteristics Of the Silicone rubber surface against the rotatable metal insert by a reduction in the friction provided by a treatment of the silicone rubber surface comprising a plasma discharge which is provided inside the passageway.

2. The device of claim 1 wherein the modified silicone rubber surface includes a coating formed on the silicone rubber surface by the plasma discharge treatment.

3. The device of claim 2 wherein the coating is provided by a polymerizable vapor in the plasma discharge.

4. The device of claim 1 wherein the passageway has a diameter of less than about 1 millimeter.

5. The device of claim 1 wherein the friction is reduced by a reduction in the coefficient of sliding friction by at least 40%.

6. In a body implantable flexible lead assembly for electrical transmission to body tissue having an elongated polymeric insulator, an electrode at a distal end thereof adapted for engaging tissue upon being rotated for fixation thereto, an elongate conductor extending longitudinally within a passageway defined by the insulator and co-extensive therewith, said passageway having an inner surface with the inner surface having a friction against the conductor, means for connecting a distal end of the conductor to the electrode whereby rotation of the conductor at a proximal end causes rotation of the electrode for fixation, the improvement comprising:

the passageway having the friction reduced on the inner surface thereof to facilitate rotation of the conductor therein, the reduction of the friction being provided by glow discharge treatment provided inside the passageway.

7. The lead of claim 6 wherein the conductor is a torsionally wound electrical coil conductor.

8. The lead of claim 6 wherein the insulator is of silicone rubber.

9. The lead of claim 6 wherein a coating on the inner surface is provided by a polymerizable vapor in the plasma discharge.

10. The lead of claim 6 wherein the passageway has a diameter of less than about 1 millimeter.

11. The lead of claim 6 wherein the friction is reduced by a reduction in the coefficient of sliding friction by at least 40%.

\* \* \* \* \*